United States Patent
Hsu et al.

(10) Patent No.: US 10,366,779 B2
(45) Date of Patent: Jul. 30, 2019

(54) SCHEME OF NEW MATERIALS (71) Applicant: INTERNATIONAL BUSINESS MACHINES CORPORATION, Armonk, NY (US)

(72) Inventors: Hsiang H. Hsu, Kanagawa (JP); Gakuto Kurata, Tokyo (JP); Koji Masuda, Kanagawa (JP); Shigeru Nakagawa, Tokyo (JP); Hajime Nakamura, Kanagawa-ken (JP); Seiji Takeda, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 315 days.

(21) Appl. No.: 14/984,989

(22) Filed: Dec. 30, 2015

(65) Prior Publication Data
US 2017/0193200 A1 Jul. 6, 2017

(51) Int. Cl.
*G01N 33/48* (2006.01)
*G01N 33/50* (2006.01)
*G16C 20/70* (2019.01)
*G16C 20/30* (2019.01)

(52) U.S. Cl.
CPC ............ *G16C 20/70* (2019.02); *G16C 20/30* (2019.02)

(58) Field of Classification Search
None
See application file for complete search history.

(56) References Cited

U.S. PATENT DOCUMENTS 7,751,988 B2 * 7/2010 Kita ................... G01N 33/6803
365/94
2004/0220749 A1 * 11/2004 Miller .................... G01N 21/25
702/19

(Continued)

FOREIGN PATENT DOCUMENTS

JP 2006236151 A 9/2006

OTHER PUBLICATIONS

Cornilescu et al. Protein backbone angle restraints from searching a database for chemical shift and sequence homology. Journal of Biomolecular NMR, vol. 13, pp. 289-302. (Year: 1999).*

(Continued)

*Primary Examiner* — Russell S Negin
(74) *Attorney, Agent, or Firm* — Tutunjian & Bitetto, P.C.; Vazken Alexanian (57) ABSTRACT

A method and system are provided for predicting chemical structures. The method includes receiving, at a user interface, intended structural feature values and intended chemical property values, as vectors. The method further includes constructing, by a hardware processor, a prediction model, wherein the prediction model predicts other structural feature values from the intended structural feature values and the intended chemical property values, and automatically configuring, by the hardware processor, at least one chemical structure candidate from the other structural feature vectors. The method additionally includes evaluating the at least one chemical structure candidate to determine structural feature values and chemical property values of the at least one chemical structure candidate and performing, by the hardware processor, machine learning of a chemical structure predicting system based on the evaluated structural feature values and the evaluated chemical property values of the at least one chemical structure candidate.

20 Claims, 6 Drawing Sheets

(56) References Cited

U.S. PATENT DOCUMENTS

| | | | |
|---|---|---|---|
| 2008/0310697 A1* | 12/2008 | Razifar | G06T 5/002 |
| | | | 382/131 |
| 2010/0145896 A1 | 6/2010 | Yuta | |
| 2010/0191517 A1* | 7/2010 | Blundell | G06F 19/16 |
| | | | 703/11 |
| 2013/0041638 A1 | 2/2013 | Nagahori | |
| 2013/0252280 A1 | 9/2013 | Weaver et al. | |
| 2015/0134315 A1 | 5/2015 | Sarmiento et al. | |
| 2017/0323085 A1 | 11/2017 | Wu et al. | |

OTHER PUBLICATIONS

Giguere, S. et al., "Machine Learning Assisted Design of Highly Active Peptides for Drug Discovery," PLOS Computational Biology, Apr. 2015. (pp. 1-21).

Liu, R. et al., "A predictive machine learning approach for microstructure optimization and materials design," Scientific Reports, Jun. 2015. (pp. 1-12).

Nagamochi Laboratory, "Study of Algorithms for Estimation Problem of Chemical Graph," Kyoto University Age Zhao Laboratory, Retreived Dec. 2015. (pp. 1-3).

Toyohashi University of Technology, "Takahashi Yukarimasashi (Takahashi Yoshikazu)," Toyohashi University of Technology, Retrieved Dec. 2015. (pp. 1-3). Available at http://www.tut.ac.jp/university/faculty/cs/315.html.

Uemura, K. et al., "Proposal of New Catalysts Using Chemoinformatics Method," Journal of Computer Aided Chemistry, vol. 7, Jul. 2006. (pp. 1-10).

\* cited by examiner

SCHEME OF NEW MATERIALS

BACKGROUND

Technical Field

The present invention relates to chemical structure design and more particularly to designing chemical structures that can possess multiple intended chemical and physical properties.

Description of Related Art

The combination of chemical elements to produce new elemental compounds has long been researched through experimentation and study. As new chemical compositions are discovered, the physical and chemical properties of the compositions are analyzed. Many of these physical and chemical properties have been found, in one form or another, to be beneficial.

Until this point in time, there have only been roughly $10^9$ discovered materials. When compared to the more than $10^{62}$ materials yet to be discovered, the number of discovered materials is only a very small fraction of the total amount of possible materials. These yet to be discovered materials could possess a vast amount of beneficial physical and chemical properties. However, not every material possesses beneficial physical and chemical properties. Therefore, there is an increase in demand to for the discovery and design of new materials so that the materials with beneficial physical and chemical properties can be determined.

Conventionally, researchers and engineers had performed material design. The researchers and engineers would use their intuition and the repetition of trial-and-error experimentation and chemical simulation in order to produce new materials with new physical and chemical properties. However, these conventional methods were very time-consuming and were not conductive to the exploration and study of the vast parameter space of undiscovered materials.

Recently, machine learning has been applied in an attempt to make the discovery and design of new materials more efficient. However, most of these machine-learning methods base their reports of the predicted physical and chemical properties of materials on the structural information of the materials. This indicates that the structures of the materials must first be determined before such machine learning can take place. There are thus few reports concerning machine learning that result in the prediction of the structure of a material based on intended physical and chemical properties.

Some methods report on chemical structure prediction through regression. However, due to the nature of regression, the input and output of a regression model are constrained to be in the vector and scalar form, respectively. Therefore, in such a report, a system receives a structural feature vector and predicts its chemical feature, creating a constructed model. On the constructed model, structural feature parameters are swept in order to determine the structural parameter set that meets the intended property. By sweeping the parameter set, this grid search requires a very large amount of computation power when the parameter set has a high dimension. Furthermore, it is impossible to construct a model to predict multiple chemical features using such a system because the output is restricted to be a scalar value. Additionally, this method is limited to only inorganic materials.

Some other known methods perform chemical structure prediction of organic materials. However, such methods are limited to the prediction of a structure that possesses a chemical value that ranges only in existing materials. This is because such methods utilize a kernel method, which is based on a similarity search, to analyze chemical structures.

Therefore, there is a need for a system and method for designing chemical structures that can possess multiple intended chemical and physical properties by utilizing machine learning.

SUMMARY

According to an aspect of the present principles, a method is provided for predicting chemical structures. The method includes receiving, at a user interface, intended structural feature values and intended chemical property values, as vectors. The method further includes constructing, by a hardware processor, a prediction model, wherein the prediction model predicts other structural feature values from the intended structural feature values and the intended chemical property values, and automatically configuring, by the hardware processor, at least one chemical structure candidate from the other structural feature vectors. The method additionally includes evaluating the at least one chemical structure candidate to determine structural feature values and chemical property values of the at least one chemical structure candidate and performing, by the hardware processor, machine learning of a chemical structure predicting system based on the evaluated structural feature values and the evaluated chemical property values of the at least one chemical structure candidate.

According to another aspect of the present principles, a system is provided for predicting chemical structures. The system includes a user interface configured to receive, as vectors, intended structural feature values and intended chemical property values. The system further includes a hardware processor configured to construct a prediction model, wherein the prediction model predicts other structural feature values from the intended structural feature values and the intended chemical property values, automatically configure at least one chemical structure candidate from the other structural feature vectors, and perform machine learning of the system for predicting chemical structures based on determined structural feature values and determined chemical property values of the at least one chemical structure candidate.

These and other features and advantages will become apparent from the following detailed description of illustrative embodiments thereof, which is to be read in connection with the accompanying drawings.

BRIEF DESCRIPTION OF THE DRAWINGS

The disclosure will provide details in the following description of preferred embodiments with reference to the following figures wherein.

DETAILED DESCRIPTION

Embodiments of the present invention implement a scheme to predict new chemical structures which can be used to construct new chemical materials and molecules. The scheme utilizes both machine learning and intended physical and chemical properties. In an embodiment of the present principles, the intended physical and chemical properties are input by a user.

In an embodiment of the present principles, a chemical structure predictor predicts structural feature vectors from the intended physical and chemical properties. In an embodiment, the structural feature vectors include at least one of the number of heavy atoms, the number of ring structures, the number of double bonds, and the number of triple bonds.

In an embodiment, the chemical structure predictor constructs a prediction model by combining a dimension reduction method and a regression method and automatically configuring chemical structural candidates from the predicted structural feature vectors. In an embodiment, the dimension reduction method may include at least one of Principal Component Analysis (PCA) and a Stacked Auto Encoder (SAE).

In an embodiment, once the scheme outputs a predicted chemical structure, the predicted chemical structure is further analyzed to determine the physical and structural properties of the predicted chemical structure. Subsequent to the predicted chemical structure being analyzed, data gathered concerning the predicted chemical structure is fed back into the chemical structure predictor to enable machine learning, during which the chemical structure predictor incorporates the data into subsequent chemical structure predictions. In an embodiment of the present principles, machine learning may include recognizing potential chemical structure features and values from previously evaluated chemical structures. Since the chemical structure predictor learns from all of the data fed back into it, future chemical structure predictions are likely to be more accurate.

Figure 1:
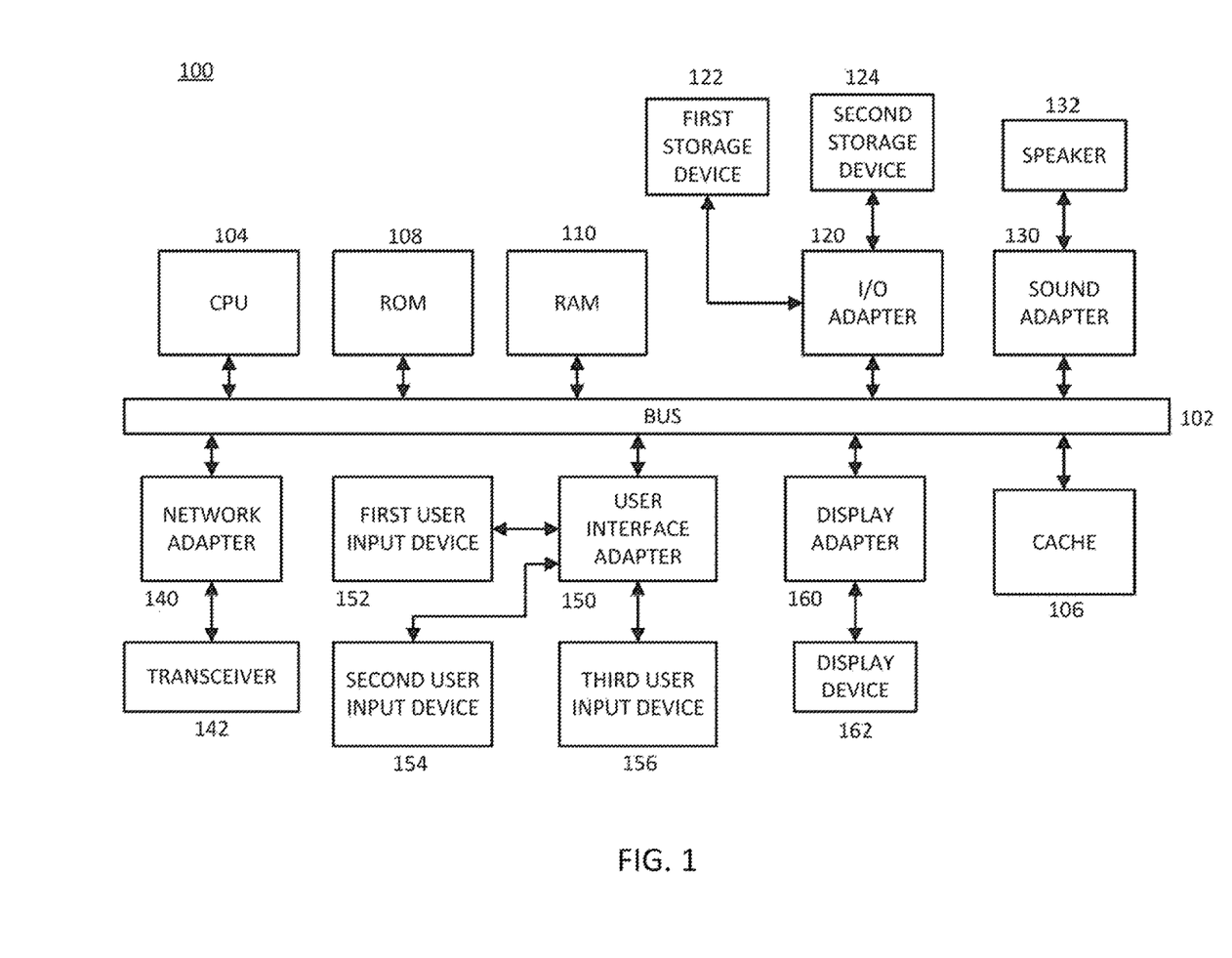
FIG. 1 shows an exemplary processing system 100 to which the present principles may be applied, in accordance with an embodiment of the present principles.

Referring to the drawings in which like numerals represent the same or similar elements and initially to FIG. 1, an exemplary processing system 100, to which the present principles may be applied, is illustratively depicted in accordance with an embodiment of the present principles. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 152, 154, and 156 can be the same type of user input device or different types of user input devices. The user input devices 152, 154, and 156 are used to input and output information to and from system 100.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present principles provided herein.

Figure 6:
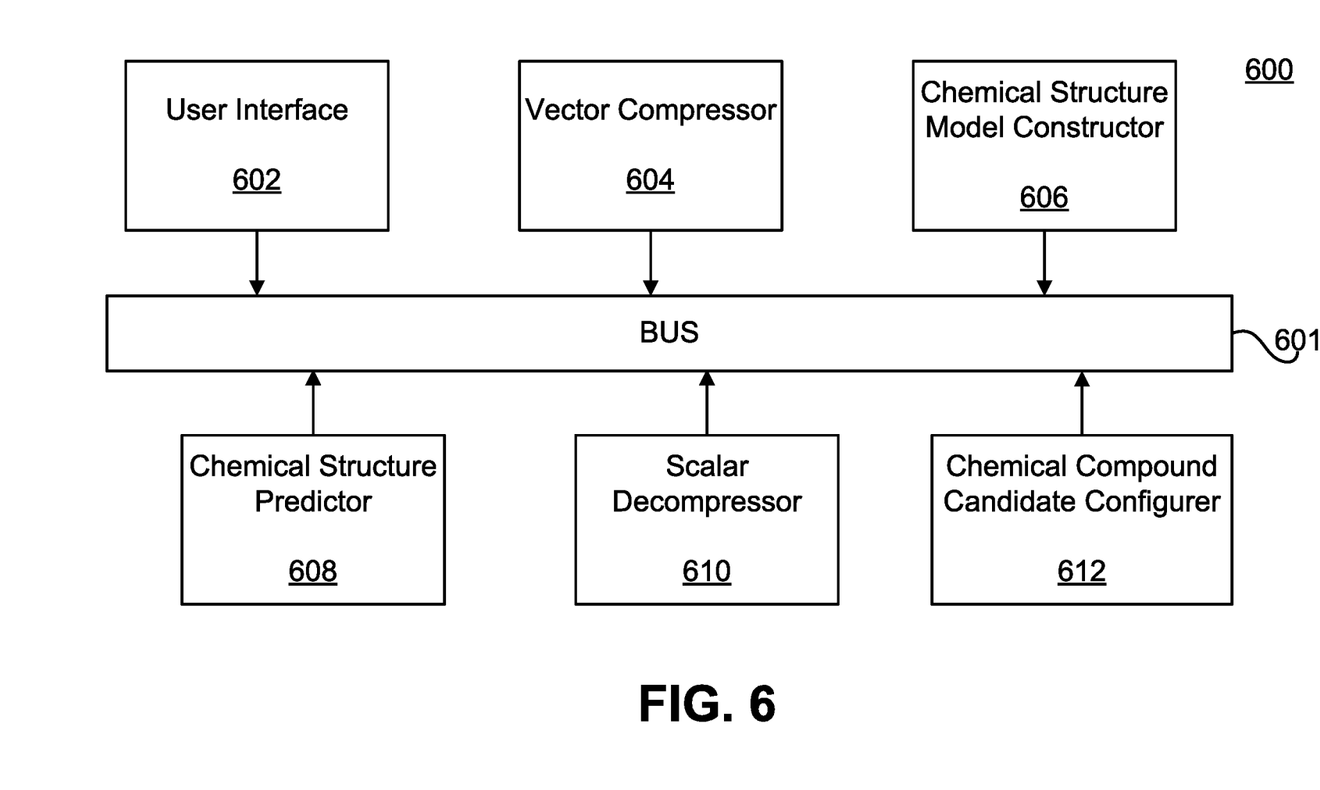
FIG. 6 shows an exemplary system 600 for predicting chemical compound candidates, in accordance with an embodiment of the present principles.

Moreover, it is to be appreciated that system 600 described below with respect to FIG. 6, is a system for implementing respective embodiments of the present principles. Part or all of processing system 100 may be implemented in one or more of the elements of system 600.

Figure 2:
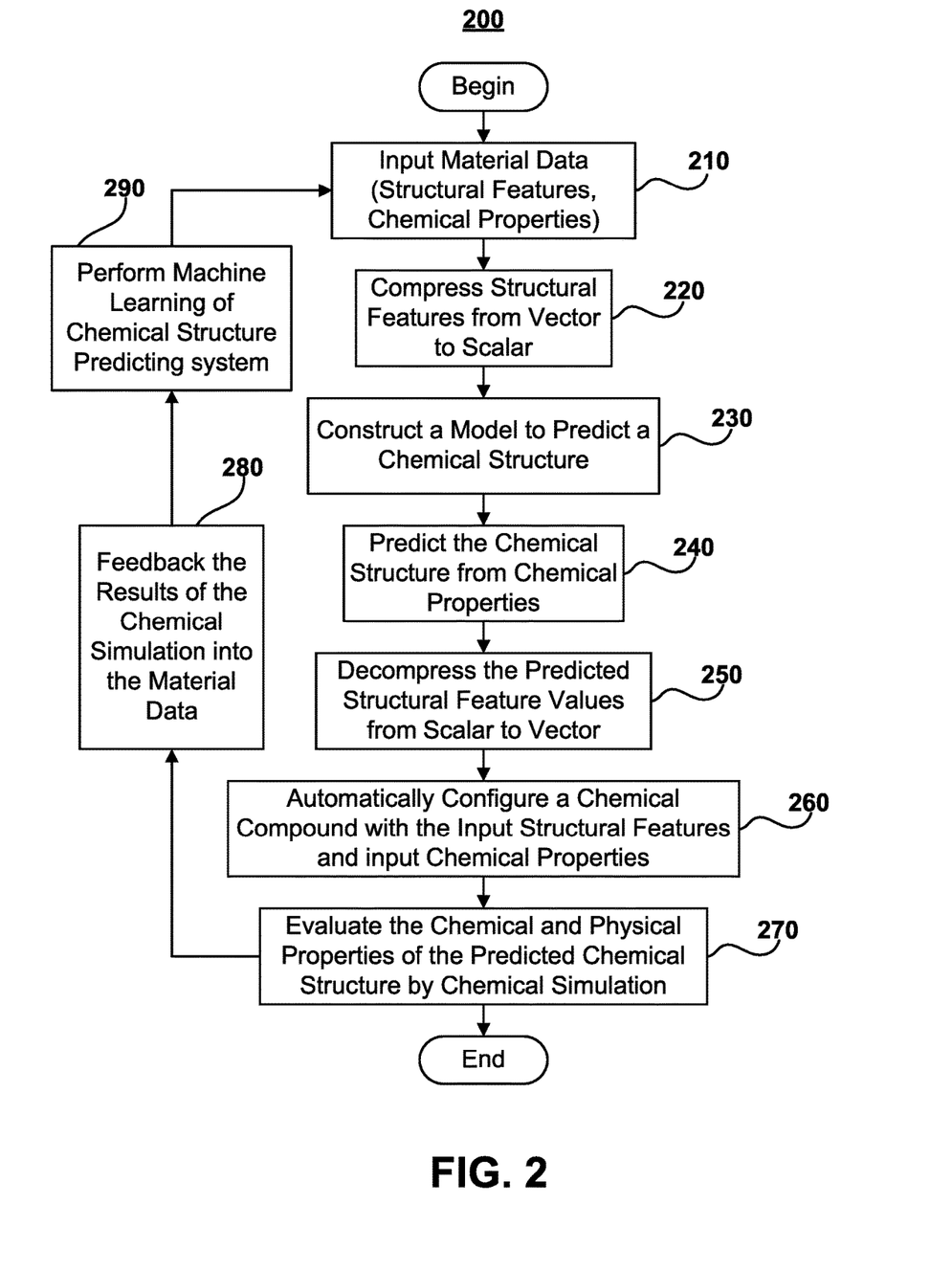
FIG. 2 shows an exemplary method 200 for predicting chemical compound candidates, in accordance with an embodiment of the present principles.

Further, it is to be appreciated that processing system 100 may perform at least part of the method described herein including, for example, at least part of method 200 of FIG. 2. Similarly, part or all of system 600 may be used to perform at least part of method 200 of FIG. 2.

Referring to FIG. 2, a flowchart of a method 200 of predicting chemical structures is shown, according to an embodiment of the present principles.

At step 210, raw material data is input into the system. In an embodiment, the raw data is input by a user. The raw material data includes at least one of intended structural feature values and intended chemical property values. In an embodiment, the raw material data is compressed and/or transformed into vectors. In an embodiment, the intended structural feature values may include the number of heavy atoms, the number of ring structures, the number of atoms of every present non-carbon element, the number of each substituent (such as —OH, —COOH, etc.), the number of double bonds, and the number of triple bonds.

At step 220, the structural features are compressed. As a result of the compression, the structural features are transformed into scalar form.

At step 230, a prediction model is constructed to predict a chemical structure from the intended chemical property values. In an embodiment, the prediction model predicts other structural feature vectors from the intended structural feature values and the intended chemical property values. The other structural feature vectors may include different structural features from the intended structural features and/or the same structural features with different values.

At step 240, the model is used to predict separate structural feature values from the intended chemical properties. In an embodiment, the predicted structural feature values are represented as scalars. In an embodiment, the model predicts the structural feature values by combining a dimension reduction method and a regression method. In an embodiment, the dimension reduction method may include at least one of Principal Component Analysis (PCA) and a Stacked Auto Encoder (SAE).

At step 250, the structural feature values are decompressed. During decompression, the predicted structural feature values are transformed into vectors by inverse PCA or SAE. In an embodiment of the present principles, the connection weights used for inverse SAE are the same connection weights as the ones used in the compression process.

At step 260, at least one chemical compound candidate is automatically configured from the predicted structural feature vectors. In an embodiment of the present principles, the chemical compound candidates are configured by manipulating Simplified Molecular-Input Line-Entry System (SMILES) strings. This process is shown in further detail in FIGS. 3A-D. Of course, other methods may be employed for configuring the chemical compound candidates, while maintaining the spirit of the present principles.

In an embodiment, after the chemical compound candidates are configured, the chemical compound candidates are visually displayed to a user. This display may be performed on a graphical user interface.

Further regarding step 260, subsequent to the machine learning of step 290, step 260 may be repeated, wherein the results of the evaluation in step 270 are used, at least in part, during the configuration of the subsequent chemical compound candidates.

In step 270, the chemical compound candidates are evaluated. In an embodiment, the evaluation process includes determining at least one of the physical properties and the chemical properties of the chemical compound candidates. This assessment is a verification of the actual chemical and physical properties of the predicted chemical structure and may be performed through chemical and physical simulation, such as first principle simulation, the Molecular Dynamics method, etc. Of course other methods of chemical and physical simulation may be performed, while maintaining the spirit of the present principles.

In step 280, once the assessment of the actual chemical structure is completed, the chemical structure's actual chemical property values and structural feature values are fed back as an appended training data set.

In step 290, machine learning is performed by incorporating the chemical structure's actual chemical property values and structural feature values. By continuously updating the system with appended training sets, the system is able to learn from prior chemical structure predictions.

Referring now to FIGS. 3A-D, chemical structures, represented by SMILES strings, formed during the chemical compound candidate automatic configuration process, are shown.

Figure 3A:
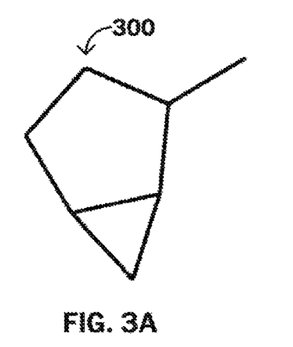
FIGS. 3A-D shows chemical structures 300-330, represented by SMILES strings, formed during a chemical compound candidate automatic configuration process, in accordance with an embodiment of the present principles.

During the automatic configuration process, the system performs several steps. FIG. 3A shows a SMILES string 300 created using the first step. During this first step, a bone structure is created out of carbon atoms, using single bonds. This bone structure is made using the intended number of heavy atoms and the intended number of rings. Of course other methods of creating the bone structure may be performed, according to aspects of the present principles.

Figure 3B:
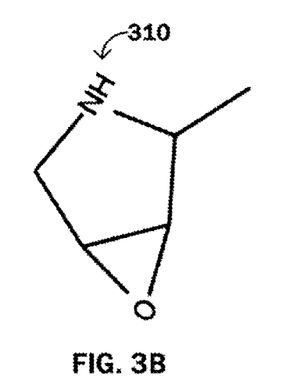

FIG. 3B shows a SMILES string 510 created using the second step. During this second step, the carbon atoms, which make up the bone structure, are replaced with other atoms. This step is performed using the intended number of atoms for each non-carbon element.

Figure 3C:
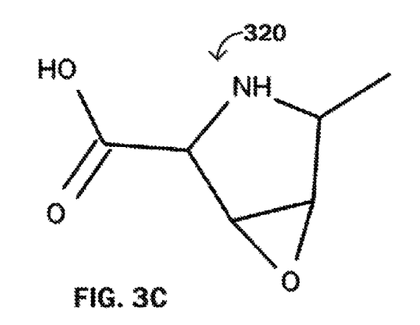

FIG. 3C shows a SMILES string 320 created using the third step. During this third step, the intended substituents (such as —OH, —COOH, etc.) are added to the structure.

Figure 3D:
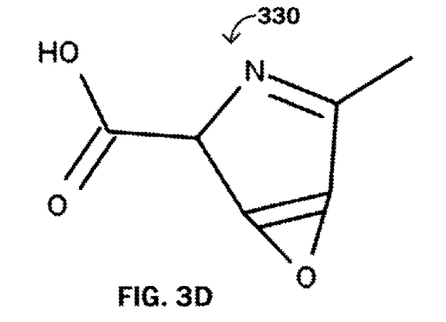

FIG. 3D shows a SMILES string 330 created during the fourth step. During this fourth step, the single bonds of the bone structure are replaced with the intended number of double and triple bonds.

After the SMILES string 330 of the fourth step is created, structures that do not satisfy the predicted structural features (such as the number of aromatic rings, etc.) are filtered out during a fifth step. Once this fifth step is completed, the SMILES structure of the chemical compound candidate is completed.

Figure 4:
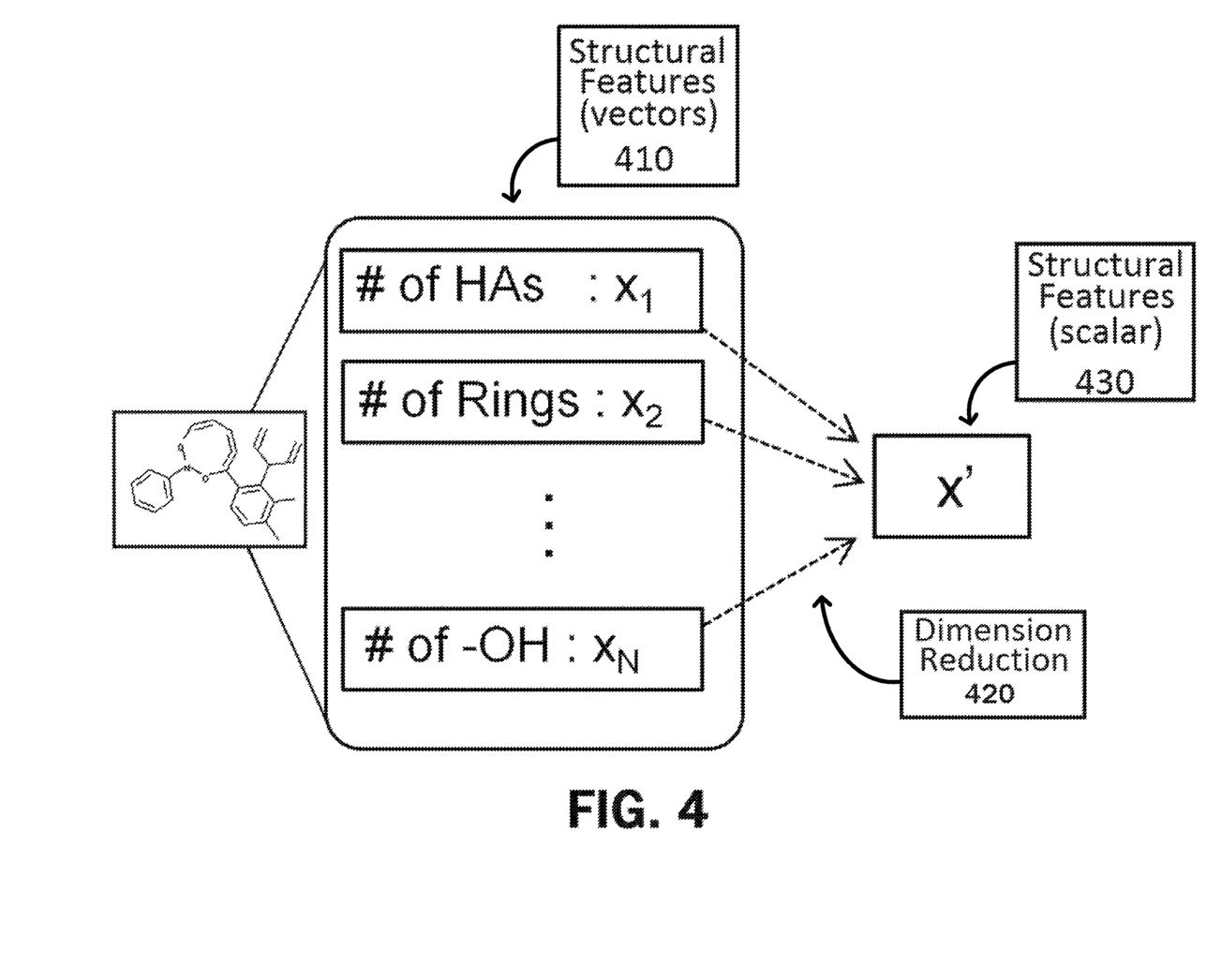
FIG. 4 shows a method 400 of the dimension reduction of structural feature vectors 410, in accordance with an embodiment of the present principles.

Referring now to FIG. 4, a method 400 of the dimension reduction of structural feature vectors 410 is shown in accordance with an embodiment of the present principles.

The method 400 includes the inputting of structural features 410 as vectors. The structural feature vectors 410 may be input by a user and may include the number of heavy atoms (# of HAs: $x_1$), the number of ring structures (# of Rings: $x_2$), the number of each non-carbon atom, the number of each constituent (such as, # of —OH: $x_N$), the number of double bonds, and the number of triple bonds. Of course, other structural features may be input by a user, according to aspects of the present principles. In an embodiment, the user inputs the structural feature vectors 410 via a user interface.

In an embodiment, once the structure feature values 410 are input as vectors, dimension reduction 420 is performed on the vectors 410. In an embodiment, the dimension reduction process 420 may include at least one of PCA and an SAE. As a result of the dimension reduction, the structural feature vectors are transformed into a scalar form 430, such as x'.

Figure 5:
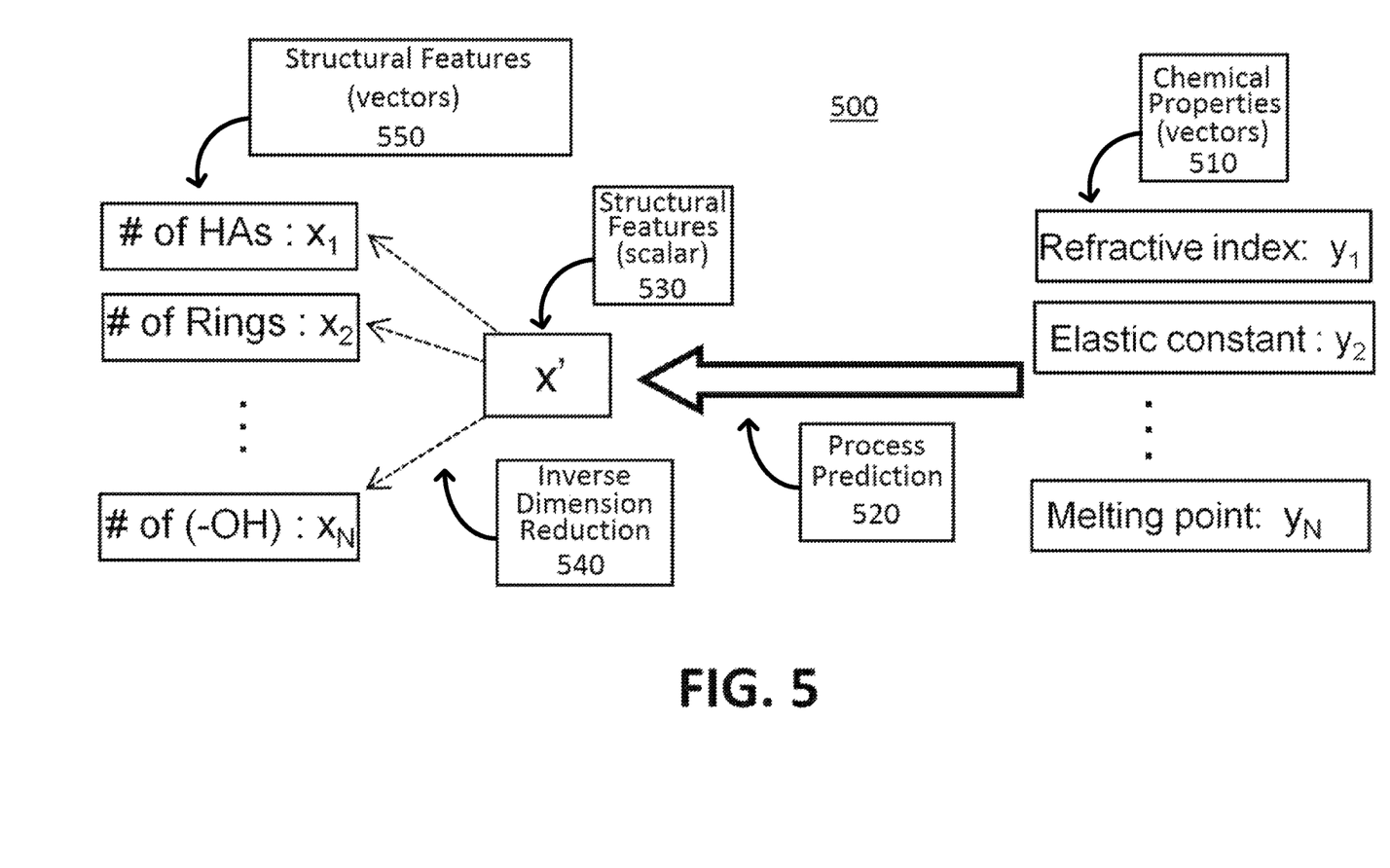
FIG. 5 shows a method 500 of model construction and prediction, in accordance with an embodiment of the present principles.

Referring now to FIG. 5, a method 500 of model construction and prediction is shown is shown in accordance with an embodiment of the present principles.

The method 500 includes the inputting of chemical property values 510 as vectors. The chemical property vectors 510 may be input by a user and may include a refractive index ($y_1$), an elastic constant ($y_2$) and a melting point ($y_N$). Of course, other chemical properties may be input by a user, according to aspects of the present principles. In an embodiment, the user inputs the chemical property vectors 510 via a user interface.

In an embodiment, once the chemical property values 510 are input as vectors, the Model & Prediction step 500 occurs. In an embodiment, a Linear or Nonlinear regression model is constructed using a training data set; a combination of vectors (x1, x2, . . . xN) (already compressed to scalar x' 530) and vectors (y1, y2, . . . yN) 510. Using the training data set, a regression model (function (g)) is constructed to satisfy x'=g(y1, y2, . . . yN). In an embodiment, the model construction process is performed by, for example, a Support Vector Machine or any other regression methods. After the regression model 520 (function (g)) is constructed, the prediction is processed 520. Users input desired values of chemical properties 510 to the regression model, g, and x' 530 is obtained as x'=g(y1, y2, . . . yN). The obtained x' 530 is decompressed, using inverse dimension reduction 540, and the structural feature vectors (x1, x2, . . . , xN) 550 are obtained (predicted).

Referring now to FIG. 6, with continued reference to FIGS. 1-5, an exemplary system 600 for predicting chemical compound candidates is illustratively depicted in accordance with an embodiment of the present principles.

The system 600 may include a user interface 602, a vector compressor 604, a chemical structure model constructor 606, a chemical structure predictor 608, a scalar decompressor 610, and/or chemical compound candidate configurer 612 according to various embodiments of the present principles.

While many aspects of system 600 are described in singular form for the sakes of illustration and clarity, the same can be applied to multiples ones of the items mentioned with respect to the description of system 600. For example, while a single user interface 602 is described, more than one user interface 602 can be used in accordance with the teachings of the present principles, while maintaining the spirit of the present principles. Moreover, it is appreciated that the user interface 602 is but one aspect involved with system 600 than can be extended to plural form while maintaining the spirit of the present principles.

In an embodiment, a user interface 602 may be employed for the inputting of raw data. The raw data may include information regarding intended structural features and chemical properties in a chemical compound. The raw data may also be inputted in vector form.

In an embodiment, a vector compressor 604 may be employed to compress the intended structural features in order to transform the intended structure features from a vector format to a scalar format.

In an embodiment, a chemical structure model constructor 606 may be employed to construct a model which can be used, by a chemical structure predictor 608, to predict a chemical structure from the intended chemical properties.

In an embodiment, the chemical structure predictor 608 may be employed to predict structural feature values from the intended chemical properties. The chemical structure predictor 608 uses the model constructed by the chemical structure model constructor. In an embodiment, the predicted structural feature values are represented as scalars. In an embodiment, the model predicts the structural feature values by combining a dimension reduction method and a regression method. In an embodiment, the dimension reduction method may include at least one of PCA and an SAE.

In an embodiment, once the structural feature vectors are determined, a scalar decompressor 610 may be employed to decompress the predicted structural feature values to transform the values from a scalar format to a vector format. In an embodiment, decompression is performed by inverse PCA or SAE. In an embodiment of the present principles, the connection weights used for inverse SAE are the same connection weights as the ones used in the compression process.

In an embodiment, a chemical compound candidate configurer 612 may be employed to automatically configure at least one chemical compound candidate from the predicted structural feature vectors. In an embodiment the chemical compound candidates are configured by manipulating Simplified Molecular-Input Line-Entry System (SMILES) strings.

In an embodiment, the at least one chemical compound candidate is evaluated to determine its chemical and physical properties. The data from this evaluation may then be input into the user interface 602 to enable machine learning by the system 600.

In the embodiment shown in FIG. 6, the elements thereof are interconnected by a bus 601. However, in other embodiments, other types of connections can also be used. Moreover, in an embodiment, at least one of the elements of system 600 is processor-based. Further, while one or more elements may be shown as separate elements, in other embodiments, these elements can be combined as one element. The converse is also applicable, where while one or more elements may be part of another element, in other embodiments, the one or more elements may be implemented as standalone elements. These and other variations of the elements of system 600 are readily determined by one of ordinary skill in the art, given the teachings of the present principles provided herein, while maintaining the spirit of the present principles.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and intended protected by Letters Patent is set forth in the appended claims.

The invention claimed is:

1. A method for predicting and designing chemical structures, comprising:
receiving, at a user interface, intended structural feature values in vector form;
receiving, at the user interface, intended chemical property values in vector form;
compressing, by a hardware processor, the vector form of the intended structural feature values into a scalar form of the intended structural feature values;
constructing, by the hardware processor, a prediction model, wherein the prediction model predicts other structural feature values in scalar form from the scalar form of the intended structural feature values and the vector form of the intended chemical property values;
automatically configuring, by the hardware processor, at least one chemical structure candidate from the other structural feature values in vector form;

evaluating the at least one chemical structure candidate to determine structural feature values and chemical property values of the at least one chemical structure candidate; and designing at least one chemical structure for constructing at least one chemical material, including performing, by the hardware processor, machine learning based on the determined structural feature values and the determined chemical property values of the at least one chemical structure candidate.

2. The method of claim 1, wherein the intended structural feature values include at least one of a number of heavy atoms, a number of ring structures, a number of non-carbon atoms, a number of constituents, a number of double bonds, and a number of triple bonds.

3. The method of claim 1, further comprising decompressing, by the hardware processor, the scalar form of the other structural feature values into the vector form of the other structural feature values, including performing inverse dimension reduction of the other structural feature values to transform the scalar form of the other structural feature values from the scalar form to the vector form, and wherein the inverse dimension reduction comprises at least one of inverse Principal Component Analysis and a Stacked Auto Encoder.

4. The method of claim 1, wherein the prediction model is constructed by combining a dimension reduction method and a regression method.

5. The method of claim 4, wherein the dimension reduction method comprises at least one of Principal Component Analysis and a Stacked Auto Encoder.

6. The method of claim 1, wherein the at least one chemical structure candidate is constructed by manipulating Simplified Molecular-Input Line-Entry System strings.

7. The method of claim 6, further comprising visually displaying the at least one chemical structure candidate on a display device.

8. The method of claim 1, wherein the chemical properties of the at least one chemical structure candidate are evaluated using at least one of a first principle simulation and a Molecular Dynamics method.

9. A computer program product for predicting and designing chemical structures, the computer program product comprising a non-transitory computer readable storage medium having program instructions embodied therewith, the program instructions executable by a computer to cause the computer to perform a method comprising:

receiving, at a uses interface; intended structural feature values in vector form;

receiving, at the user interface, intended chemical property values in vector form;

compressing, by a hardware processor, the vector form of the intended structural feature values into scalar forms of the intended structural feature values;

constructing, by the hardware processor, a prediction model, wherein the prediction model predicts other structural feature values in scalar form from the scalar form of the intended structural feature values and the vector form of the intended chemical property values;

automatically configuring, by the hardware processor, at least one chemical structure candidate from the other structural feature values in vector form;

evaluating the at least one chemical structure candidate to determine structural feature values and chemical property values of the at least one chemical structure candidate; and designing at least one chemical structure for constructing at least one chemical material, including performing, by the hardware processor, machine learning based on the determined structural feature values and the determined chemical property values of the at least one chemical structure candidate.

10. The computer program product of claim 9, wherein the intended structural feature values include at least one of a number of heavy atoms, a number of ring structures, a number of non-carbon atoms, a number of constituents, a number of double bonds, and a number of triple bonds.

11. The computer program product of claim 9, wherein the method further comprises decompressing, by the hardware processor, the scalar form of the other structural feature values into the vector form of the other structural feature values, including performing inverse dimension reduction of the other structural feature values to transform the scalar form of the other structural feature values from the scalar form to the vector form, and wherein the inverse dimension reduction comprises at least one of inverse Principal Component Analysis and a Stacked Auto Encoder.

12. The computer program product of claim 9, wherein the prediction model is constructed by combining a dimension reduction method and a regression method, and wherein the dimension reduction method includes at least one of Principal Component Ana and a Stacked Auto Encoder.

13. A system for predicting and designing chemical structures, comprising:

a user interface configured to receive, in vector form, intended structural feature values and intended chemical property values; and a hardware processor configured to:
compress the vector form of the intended structural ur values into a scalar form of the intended structural feature values;
construct a prediction model, wherein the prediction model predicts other structural feature values in scalar form from the scalar form of the intended structural feature values and the vector form of the intended chemical property values;
automatically configure at least one chemical structure candidate from the other structural feature vectors in vector form;
evaluate the at least one chemical structure candidate to determine structural feature values and chemical property values of the at least one chemical structure candidate; and
design at least one chemical structure for constructing at least one chemical material by performing machine learning based on the determined structural feature values and the determined chemical property values of the at least one chemical structure candidate.

14. The system of claim 13, herein the intended structural feature values include at least one of a number of heavy atoms, a number of ring structures, a number of non-carbon atoms, a number of constituents, a number of double bonds, and a number of triple bonds.

15. The system of claim 13, wherein the hardware processor is further configured to decompress the scalar form of the other structural feature values into the vector form of the other structural feature values by performing inverse dimension reduction on the scalar form of the other structural feature values to transform the other structural feature values from the scalar form to the vector form, and wherein the inverse dimension reduction comprises at least one of inverse Principal Component Analysis and a Stacked Auto Encoder.

16. The system of claim 13, wherein the hardware processor is further configured to construct the prediction model by combining a dimension reduction method and a regression method.

17. The system of claim 16, wherein the dimension reduction method comprises at least one of Principal Component Analysis and a Stacked Auto Encoder.

18. The system of claim 13, wherein the hardware processor is further configured to construct the at least one chemical structure candidate by manipulating Simplified Molecular-Input Line-Entry System strings.

19. The system of claim 18, further comprising a display device configured to visually display the at least one chemical structure candidate.

20. The system of claim 13, wherein the chemical properties of the at least one chemical structure candidate are evaluated using at least one of a first principle simulation and a Molecular Dynamics method.

* * * * *